(12) United States Patent
Hurst

(10) Patent No.: US 7,766,164 B2
(45) Date of Patent: Aug. 3, 2010

(54) MEDICAL TRAY AND COVER APPARATUS

(76) Inventor: Richard Francis Hurst, 1375 Admirals Walk, Vero Beach, FL (US) 32963

(*) Notice: Subject to any disclaimer, the term of this patent is extended or adjusted under 35 U.S.C. 154(b) by 465 days.

(21) Appl. No.: 11/200,922

(22) Filed: Aug. 10, 2005

(65) Prior Publication Data

US 2006/0071002 A1 Apr. 6, 2006

Related U.S. Application Data

(60) Provisional application No. 60/601,051, filed on Aug. 13, 2004.

(51) Int. Cl.
*B65D 85/00* (2006.01)
(52) U.S. Cl. .................... 206/370; 206/438; 206/557
(58) Field of Classification Search ............... 206/363, 206/369, 370, 372, 373, 438, 439, 557, 561, 206/565, 503, 509, 821; 422/300
See application file for complete search history.

(56) References Cited

U.S. PATENT DOCUMENTS

| | | | | |
|---|---|---|---|---|
| 5,301,807 A | * | 4/1994 | Donahue | 206/370 |
| 6,113,867 A | * | 9/2000 | Mayer | 422/300 |
| 7,309,472 B2 | * | 12/2007 | Michaelson et al. | 422/297 |

* cited by examiner

*Primary Examiner*—Jacob K Ackun, Jr.
(74) *Attorney, Agent, or Firm*—Richard M. Saccocio

(57) ABSTRACT

Medical tray and cover apparatus includes a tray body having an open top and an open front; the cover is removable and covers the tray top and front. The tray body includes a plurality of oppositely disposed grooves that provide for the insertion of closure and divider panels. The tray grooves are configured to allow the tray to be loaded with ampoules or vials without being snagged by the grooves. The trays are transparent so that its contents are visible without removing the cover. The trays are stackable with the cover in place. The trays are lockable such that the ability to stack the trays is not interfered with. The tray and cover eliminate particle generation from use and wear that can contaminate the contents of the tray. The tray and cover are capable of being autoclaved.

12 Claims, 5 Drawing Sheets

MEDICAL TRAY AND COVER APPARATUS

CROSS REFERENCE TO RELATED APPLICATIONS

This application is related to U.S. Provisional Application Ser. No. 60/601,051, filed on Aug. 13, 2004.

BACKGROUND OF THE INVENTION a. Field of the Invention

This invention relates in general to the field of material handling equipment and in particular to medical material handling apparatus and more particularly to the construction of a tray and cover for primary use in the medical field.

b. Description of the Prior Art

There exists a problem in the prior art in the efficient, sterile and convenient storage and transfer of various medical equipment, drugs, specimens, vials, and other such medical paraphernalia and materials. In the past a simply constructed fiberglass tray having a bottom with four sides extending upward therefrom has been employed for the storage and transfer of the described medical materials. Such simply constructed trays usually have an open top.

One problem associated with the prior art trays is that the fiberglass generates small particles that can contaminate whatever is being stored in the trays. Continual usage and transfer of the trays exacerbate the particle generation and resulting contamination problem. Decontamination of the prior art fiberglass trays by the generally known and used methods in the medical field can cause deterioration of the fiberglass and make it more susceptible to the particle generation problem. For example, both usage and decontamination can cause deterioration of the fiberglass finish coat exposing the glass and resin under the finish coat which can then result in particles of glass and resin. Equally important is that prior art fiberglass trays have been known to fracture. Even a small fracture during usage can generate talc, resin, glass and other particles that can and will contaminate the interior of the prior art trays and the contents within the tray Additional problems are associated with the prior art trays is that the open top does not prevent the entrance of other contaminates and does not provide for security and/or tamper evidence of the materials being stored in the trays.

Another prior art tray comprises the tray being made from stainless steel. While stainless steel trays do provide for decontamination and are generally superior to fiberglass trays, they are expensive, heavy and can generate metallic particles. Moreover, if stainless steel trays incorporate a provision for stacking one on top of another, they become especially expensive.

Thus, there exists the need for a tray construction that allows for convenient, secure, ready accessibility to the interior thereof, that lessens the problem of contamination, that allows for decontamination without deterioration of the tray itself, and that can be used with a transfer cart, or that can be used for general purposes. These needs have been a long standing problem in the prior art which are overcome by the present invention.

SUMMARY OF THE INVENTION

The present invention accomplishes the above-stated objectives as well as others, as may be determined by a fair reading and interpretation of the entire specification herein including the drawings and the claims, which comprises a unique medical storage and transfer tray having a storage member, a removable front side, and a cover member. In a preferred embodiment, the storage member includes a bottom surface, two vertical side members connected to a vertical back member, and a removable front member. The cover member includes a vertical front member connected to a top member with the front member having an inwardly extending bottom edge. In another embodiment, one or more dividing members are provided to divide the space within the inventive tray into one or more discrete compartments. Other unique features are described in the following description of the preferred embodiments.

BRIEF DESCRIPTION OF THE DRAWINGS

Various other objects, advantages, and features of the invention will become apparent to those skilled in the art from the following discussion taken in conjunction with the following drawings, in which.

DESCRIPTION OF THE PREFERRED EMBODIMENTS

Figure 1:
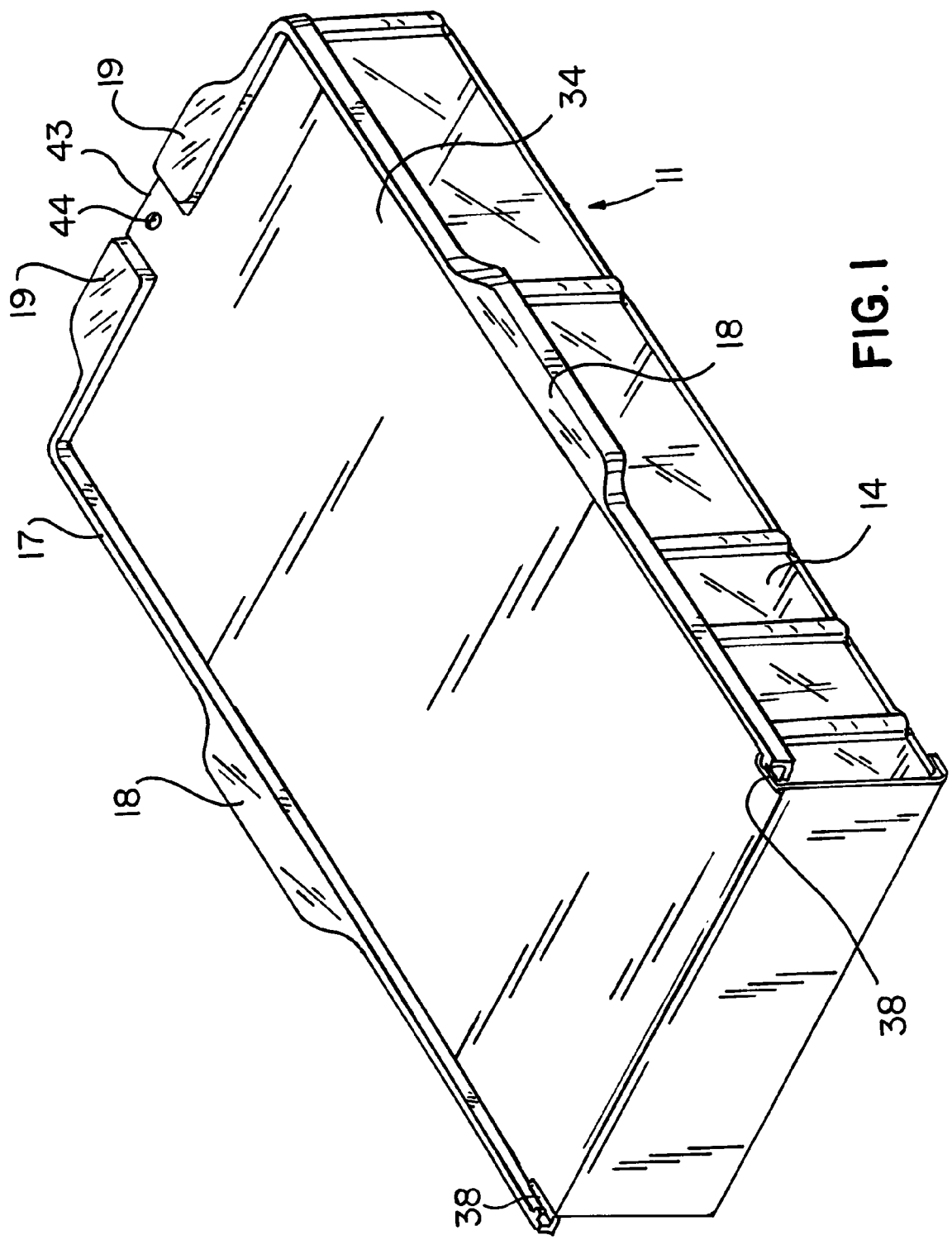
FIG. 1 is an isometric rendering of the storage member comprising the inventive tray.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

Reference is now made to the drawings, wherein like characteristics and features of the present invention shown in the various figures are designated by the same reference numerals.

Figure 2:
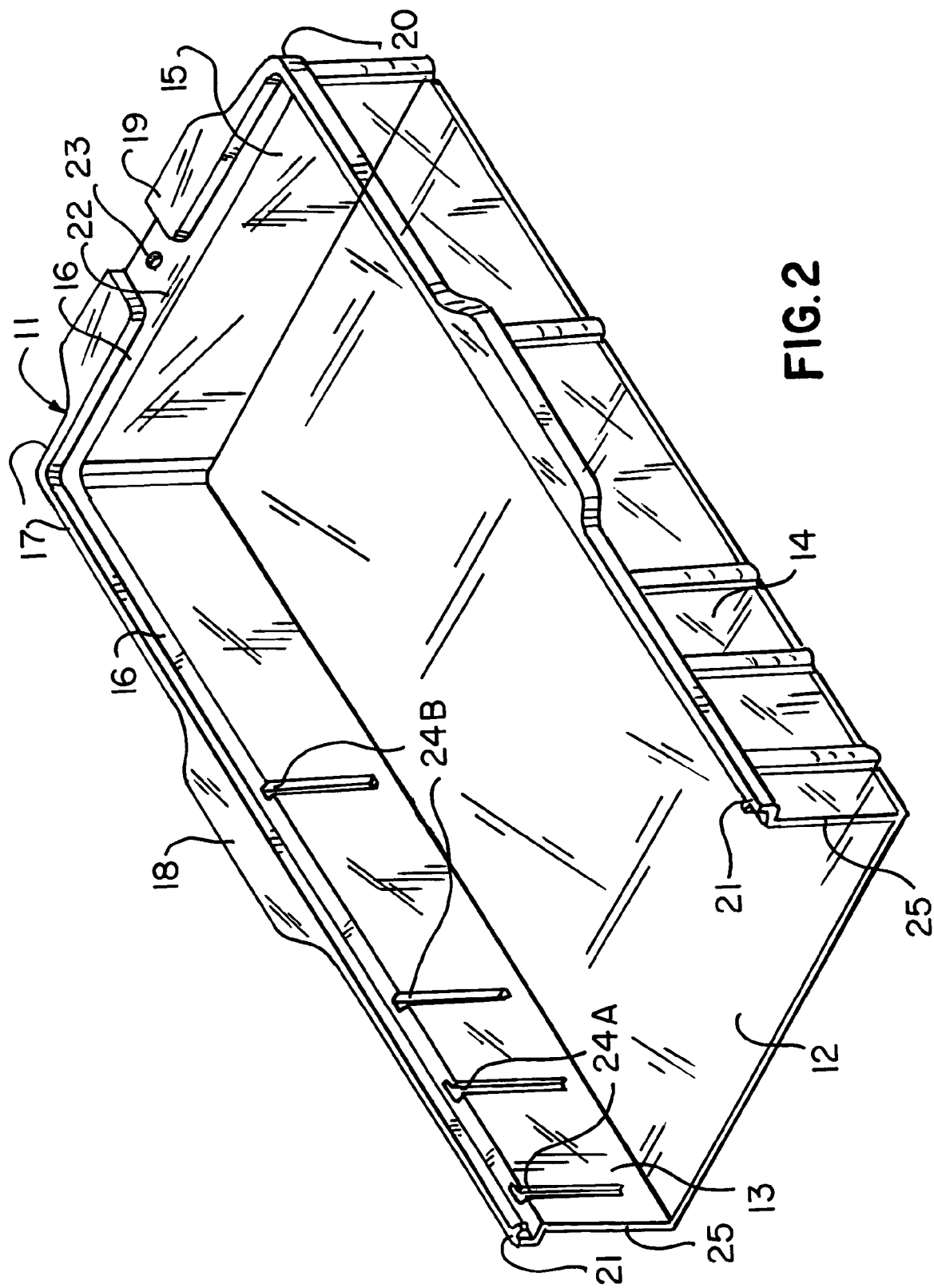
FIG. 2 is an isometric view of the body of the storage member or tray showing various details of the tray body.

Reference is now made to FIGS. 1 and 2 which comprise an isometric view of the inventive tray apparatus 10 comprising the tray body 11 having a cover 34 attached thereto, and an isometric view of the tray body 11, respectively. The tray body 11 includes a bottom 12, one side member 13, an opposite side member 14, and a back member 15; the back and side members being integrally attached to the bottom 12 along a horizontal edge thereof such that an open three sided box like structure is formed. The actual dimensions of the box-like structure are of course not critical to the invention. However, for purposes of explanation and as an example, the body 11 may be approximately 18 inches in depth, approximately 12 inches in width, and approximately five inches high. In a preferred embodiment, the box-like structure or body 11, is formed from clear or transparent, rigid plastic that is injection molded in one piece. The transparency allows any objects stored in the inventive apparatus to be viewed without the necessity of having to open the tray 10. In order to assist in automatic or machine assisted loading of a plurality of vials, ampoules or other such objects, it is preferable that the top surface of the bottom member 12 be provided with a friction reducing medium or a physical surface treatment such an embossment having rounded edges that allow vials or ampoules to easily slide there along when for example the vials or ampoules are mass loaded into a tray by a pushing technique.

It is preferred that the plastic material from which the body 11 of the tray 10 is made comprises injectable plastic, for example a polycarbonate, that is not filled with a material such as fiber glass or other particle generating filler. Non-filled injectable plastic completely eliminates the prior art problem of talc, glass, resin and metallic particles being generated by use, handling, transfer and decontamination of the tray. Additionally, injection molding allows for substantially parallel inside and outside surfaces of the walls of sides 13, 14 and back member 15 of the tray 10 and substantial perpendicularity with the bottom member 12. Such parallelism and perpendicularity further allows for close toleranced and convenient attachment of a front 28A and intermediate or dividing 28B panels and cover 34 to the tray body 11 that is important for safe storage and proper insertion and arranging of small diameter vials and ampoules within the tray 10. The plastic material can also be specially adapted to accommodate different needs, e g. general storage trays, autocavable trays, and trays exposed to sub freezing temperatures. Suitable plastics include but are not limited to polyphenylsulfone and polycarbonate S X, the latter being available from the General Electric Company.

Plastic trays are preferred because of further advantages associated with plastic, i.e. it allows for color coding, allows for venting perforations that do not generate particles, and any plastic particles that are generated do not comprise medical contamination.

The tops of the side members 13, 14 and the back member 15 are provided with a ledge 16 that extends around and internal to the side and back members and is located an appropriate distance below the top edges 17 of a rim 20. (See FIG. 2) The ledge 16 stops a small distance from the front edges 25 of sides 13 and 14 so as to form a small lip or protruding member 21 that in combination with the rim 20 of the back member provides front to rear containment of another tray 10 when stacked on the ledge 16 of a first tray 10. Side to side containment being obtained by inside edges of the rim 20 of sides 13 and 14 directly above the ledge 16. The bottom of each tray 10 is configured to fit within the ledge 16 of another tray 10 such as by providing another rim or footer that fits within the rim 20. The ledge 16 further provides a surface for fitting a cover member to the tray body 11 so as to completely enclose the tray 10.

The top edges 17 of the rim 20 of the side members 13, 14 can be provided with elongated members 18 that extend outwardly in the direction of top edge 17 for an appropriate distance and serve as handles to allow lifting or otherwise moving of the tray 10. The back member 15 is likewise provided with an extending handle member 19 which is further provided with a slot or groove 22 at the approximate center of handle 19, the bottom surface of the groove 22 being positioned to lie in the plane of the ledge 16. An opening 23 is provided through the bottom surface of groove 22 within the extending portion of handle 19.

Each side 13 and 14 is provided with a plurality of pairs of vertical grooves 24 (relative to the bottom member) spaced along the inner surface of each side 13 and 14. Each groove 24 of each pair of grooves being located opposite each other such that the distance from the front edge 24 of sides 13 and 14 of each pair of grooves is the same. One or more of the grooves 24 can have an "L" shaped cross sectional configuration 24A. Others can have "U" shaped cross sectional configuration 24B. Preferably, the first one or two pairs of grooves 24A, back from the front edges 25 of sides 13 and 14, have the "L" configuration. The different configurations of grooves 24A and 24B are shown in FIG. 2.

The grooves 24A and 24B do not extend to the bottom member 12, but rather stop a short distance above the bottom member 12 where the bottom of the grooves intersect with the inside surface of sides 13 and 14. The purpose of the non continual length of grooves 24A and 24B is to provide a flush surface directly below the grooves that comprises the interior surface of sides 13 and 14. A flush surface is important when small vials or ampoules are being loaded into the tray 10. In this way, the small vials or ampoules do not hang up within the grooves or are affected in their movement by the edges of the grooves.

FIG. 2 illustrates the outer surface of side 14 and applies equally to the outer side of side 13. The wall of sides 13 and 14 are relatively thin and can approximately equal the width of ledge 16 and such that the rim 20 extends outward from the walls. A plurality of ribs 32 is provided at the location of the grooves 24 on the outside of sides 13 and 14 in order to provide stiffness to sides 13 and 14 and to maintain the relative thinness of the walls of sides 13 and 14. In this manner, the tray body 11 is able to be made stiff but relatively light in weight. Moreover, the ribs 32 allow the depth of the grooves 24 to exceed the thickness of the walls of sides 13 and 14. Additional reinforcing ribs can be provided at the corners of tray body 11.

Figure 3:
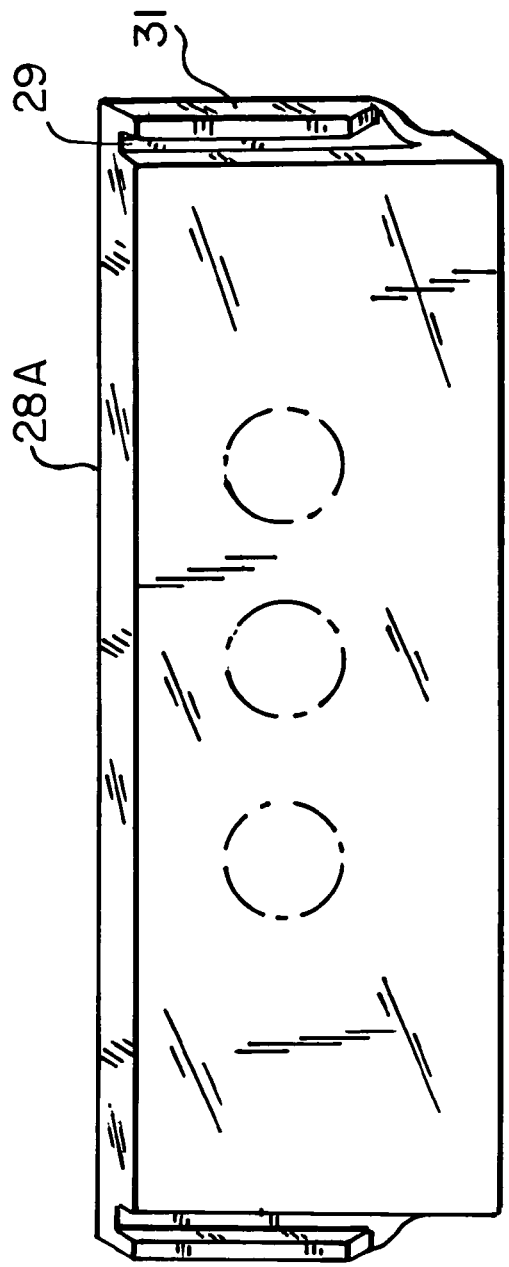
FIG. 3 is an isometric illustration of a removable front member of the tray.

FIG. 3 shows a front member or panel 28A that is preferably fitted to the grooves 24A in sides 13 and 14 having the "L" shaped configuration. Front member 28A is a separate part from tray body 11. Front member 28A is also clear or translucent and can be injection molded from a rigid type of plastic having features as described above. Front member 28A essentially comprises a planer member having a pair of "U" shaped slots or grooves 29 in the front or back surface thereof and extend in a vertical direction and located at a small distance inward from the ends 31. Front member 28A is intended to be removably attached to the tray body 11 such that it forms the front side of the tray 10. The bottom portion 30 of the ends 31 is cut away so as to effectively eliminate the groove 29 at the cut away portion 30. Thus, grooves 29 do not extend to the bottom edge of front member 28A but stop at the beginning of the cut away portion 30. The combination of the non-grooved portion 30 and the non-continuous length of grooves 24A allow the front member 28A to be inserted in grooves 24A and yet allow the bottom edge of front member 28A to come in contact with and rest on the upper surface of tray bottom 12. In other words the unique configuration of grooves 24A and 29 allow the front panel 28A to be inserted in grooves 24A for the full height of the sides 13 and 14 and for the full height of front panel 28A such that the top edge of front panel 28A substantially lies in the plane of ledge 16 and the bottom edge of panel 28A rests on the upper surface of bottom member 12.

Figure 4:
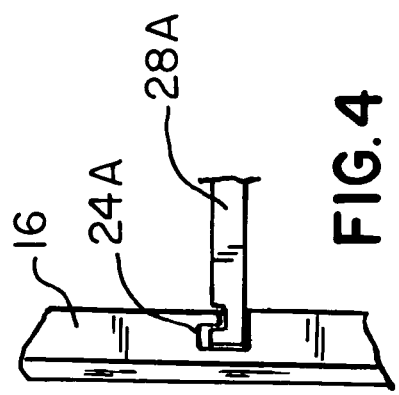
FIG. 4 is a partial view of the fit up of the front member to an "L" shaped groove in a side member.

FIG. 4 illustrates a top view of the front panel 28A fitted to an "L" shaped groove 24A in a side member 13 or 14.

Although FIG. 4 illustrates such attachment as applied to one side 13 or 14 of tray body 11, it is to be understood that the same attachment applies to the opposite side. In installing the front member 28A, the "U" shaped grooves 29 of the front member 28A are aligned with the "L" shaped grooves 24A in the side members 13 and 14 and inserted in a downward direction until the bottom edge meets with the top surface of bottom member 12. The interlocking fit up of the front member 28A with the side members 13 and 14, shown in FIG. 4, results from the configurations 24A and 29 of the respective grooves, and provides further structural rigidity to the tray 10. While some clearance space is necessary between the interlocking grooves 24A and 29 in order to assemble the two members, modern injection molding can allow for tight or close tolerances that provide for very small clearances such that upon assembly, a relatively rigid structure of the tray 10 is effectuated. Additional rigidity can be obtained by utilizing the same interlocking fit up by fitting a second removable panel 28A in a second pair of "L" shaped grooves 24A located an appropriate distance toward the back side of body 11 and spaced from the first panel 28A.

Figure 5:
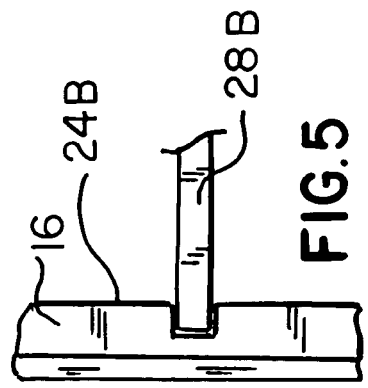
FIG. 5 is a partial view of the fit up of a tray dividing member to a "U" shaped groove in a side member.

One or more front to rear space dividing panels 28B can be incorporated in the tray 10. In a simpler embodiment, as partially shown in FIG. 5, the dividing panels 28B do not have the interlocking fit up as the front one or two panels 28A. The dividing panels 28B can simply comprise a planer member without any grooves that fit within the "U" shaped grooves 24B in side members 13 and 14. The "U" shaped grooves 24B are also non-continuous in length as with the grooves 24A. The dividing panels 28B do however incorporate the cut away portion 30 in the same manner as per the front panel 28A. Thus, as with the front panels 28A, the top edge of the dividing panels 28B lies in the plane of the ledge 16 when the dividing panels 28B are fully inserted in the tray body 11, and the bottom edge of the panel 28B rests on the upper surface of tray bottom 12.

The front to rear space between two interlocking panels 28A, or an interlocking panel 28A and a non-interlocking panel 28B, can be further divided into side to side spaces by providing full length grooves 24C in the front and or back surfaces of the panels 28A and or 28B. and inserting a plain panel 28C in the grooves 24C. The cross sectional configuration of grooves 24C can either be the "L" or the "U" shaped configuration. Thus, the side to side dividing panels 28C and the grooves 24C do not incorporate the cut away portion 30. Rather the side edges of panels 28C and their respective grooves 24C extend the full height of the panels.

The divided interior spaces in tray 10 are of course intended be used for storage and to allow separation of different types of vials and other medical paraphernalia. This feature allows for a plurality of separate compartments within a single tray 10. For example, the divided spaces can be sized to fit vial receiving stands that contain vials in a particular order and location. Additional uses for the inventive tray 10 and the divided spaces can be readily envisioned.

Front panels or members 28A and or dividing panels 28b can be provided with one or more openings through the face of the panels. This feature is shown in phantom in FIG. 3. The openings which can be square, rectangular or round, can allow for access into the tray 10 or its divided compartments when the front panel 28A or dividing panels 28B are inserted in place in to tray body 11.

Figure 6:
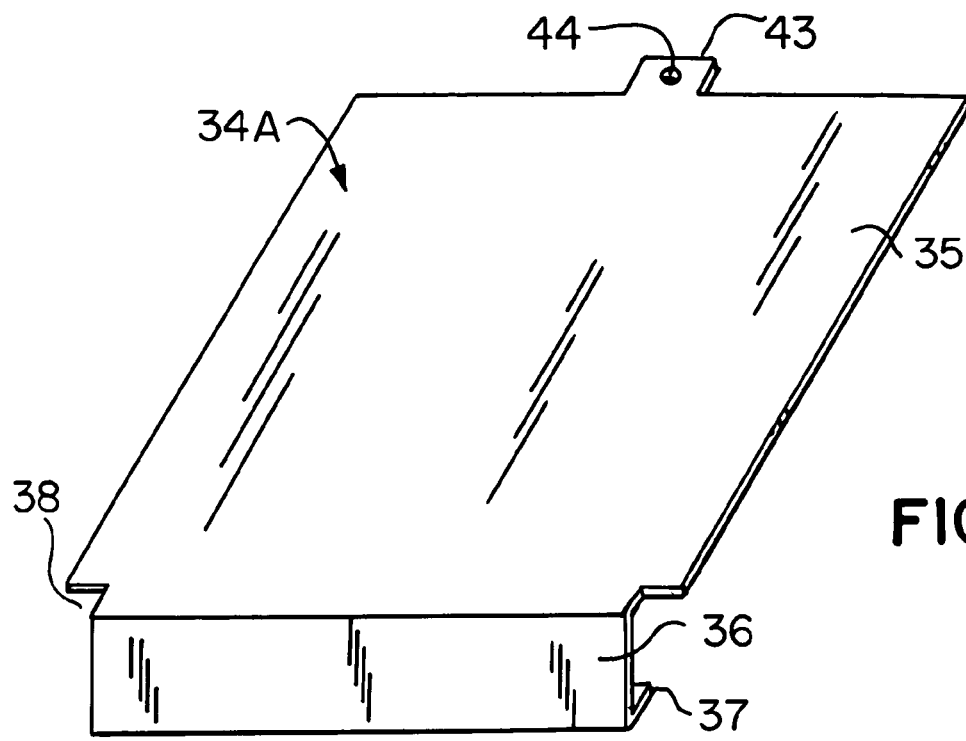
FIG. 6 is an isometric drawing of one embodiment of the cover member.

A cover 34 for the inventive tray 10 is shown in FIG. 6. In one embodiment, the cover 34A is preferably made from stainless steel sheet metal formed to include a planer top member 35 and a planar front member 36 The cover 34A is appropriately dimensioned such that the top member 35 rests on the ledge 16 (provided at the top of the sides 13 and 14 and back members 15) and within the rim 20, thereby covering the open top of tray body 11 while the front member 36 fits over the open front of tray body 11. In this manner the inventive tray 10 is completely encased and any medical paraphernalia contained therein is free from possible contamination. In a further embodiment 34B of a stainless steel cover, another planer member 37 extends a relatively short distance from the bottom of the front member 37 back in the direction of and parallel to top member 35. The purpose of the backwardly extending planer member 37 is to fit under the front edge of the bottom 12 of tray body 11 so as to further secure the cover to the tray body 11.

The width of the top member 35 of cover 34A and 34B is slightly smaller that the distance between the outside of ledges 16 and inside the rim 20, so as to fit therebetween and rest thereon. In attaching the cover 34A or 34B to the tray body 11, the top planer member 35 is inserted in slots 32 provided below the small lips 21, which lips serve to comprise non-ledged portions of the front and top of the sides 13 and 14 of the tray body 11, and then pushed rearward until contact is made with the rim 20 of the back member 15. Both the slots 32 and the backwardly extending planer member 37, serve to prevent the covers 34A and 34B from inadvertently being lifted off the tray body 11. The cut outs 38 in the front of cover 34A and 34B provide clearance for the small lips 21.

Yet another embodiment 34C of the stainless steel cover 34 comprises a cover that is configured the same as a plastic cover 39 and attached to tray body 11 in the same manner as described below.

Figure 7:
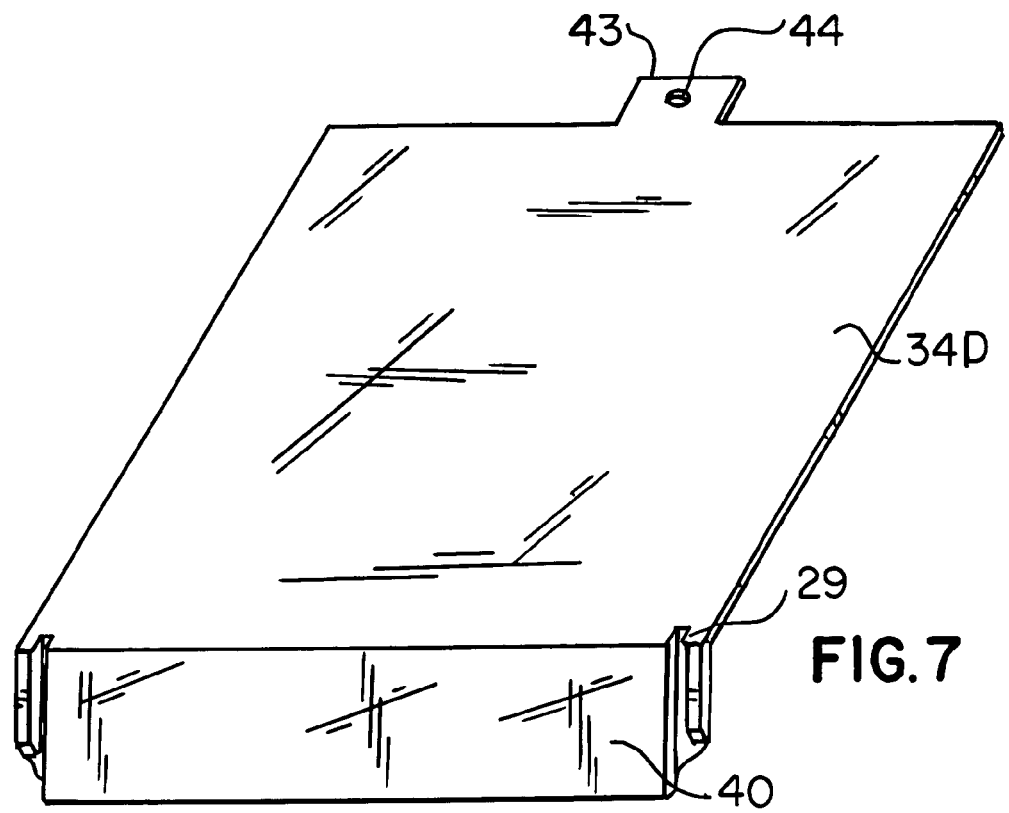
FIG. 7 is an isometric drawing of another embodiment of the cover member.
Figure 8:
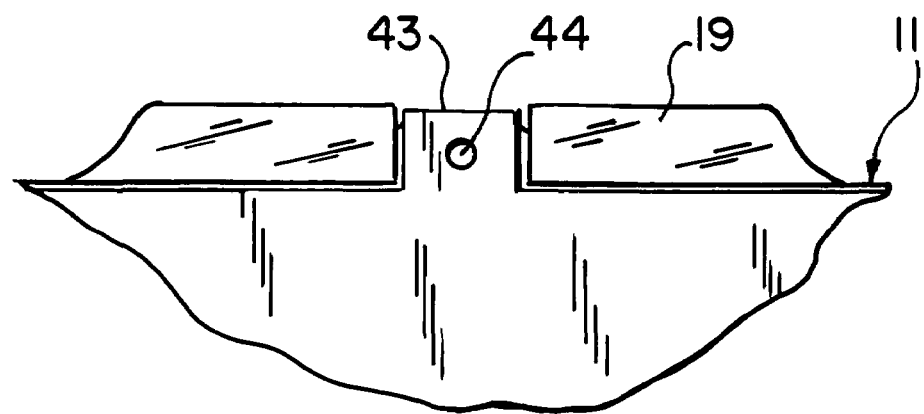
FIG. 8 is a partial top view of the lockable feature of the cover and the tray body; and, FIG. 9 is plan view of the rear of the tray and the attached cover.
Figure 9:
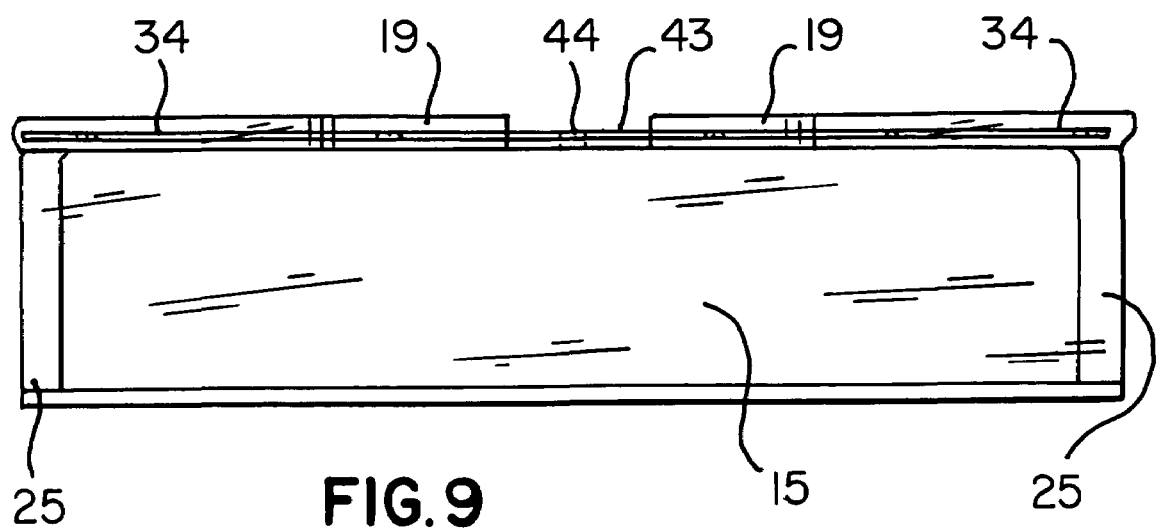

In another embodiment, a cover 34D is made from a rigid transparent or translucent plastic as described above having a top planar member 40 that is generally configured the same as top member 35 of the stainless steel embodiments so as to provide a proper fit up with the tray body 11. See FIG. 7. In this embodiment 34D, the front face 41 is provided with the "U" shaped grooves 29 and the cut away portions 30 as with the plastic front panel 28A. Thus, the grooves 29 of the plastic cover 34D fit within the "L" shaped grooves 24A in the tray body 11 and in the same manner as the front plate member 28A. In attaching the plastic cover 34D to the tray body 11, the front face member 39 is inserted in the "L" shaped grooves 24A in each side member 13 and 14 and then lowered until the top member 40 rests on the ledges 16. With the plastic cover embodiment, a front plate 28A is not used. However, if it is desired to utilize a front plate member 28A in addition to the front plate 41 of the plastic cover 34D, a second pair of "L" shaped grooves 24A can be provided in side members 13 and 14 a small distance from the first pair of "L" shaped grooves 24A, back toward the back member 15. The second pair of "L" shaped grooves 24A is then used to fit the front plate member 28A.

With all embodiments of the cover 34, an extending tab 43 having a through opening 44 at the rearmost location of cover 34 or 38 is configured to fit with the slot or groove 22 provided in the back handle 19 of back member 15 when the cover 34 is placed on the tray body 11. At this time, the through opening 44 in tab 43 aligns with the through opening 23 in the back handle 19. In this manner when the cover 34 is placed on tray body 11, a lock can be inserted in the openings 23 and 44 to prevent unauthorized entry into the covered tray 10. Moreover, with the present invention and because of the location of the lockable feature, the lock does not interfere with stacking feature of the inventive trays 10 or otherwise interfere with the containment features of the tray 10.

In a preferred embodiment the bottom external surface of bottom member 12 of tray body is provided with footer or rim that extends around the bottom member 12 and is indented a small distance so as to rest on and fit within the ledge 16 of another tray 10. In this manner, one tray 10 can be stacked on another tray 10 with the footer of the upper tray 10 resting on and fitting within the ledges 16 of the lower tray 10 and, as explained above provides for front to rear and side to side containment of stacked trays 10. In order to remove an intermediate tray 10 from a stack of trays 10, it is a simple matter to slightly lift the upper tray or trays 10 to allow the intermediate tray 10 to clear the footer from the ledge 16 and allow the intermediate tray 10 to be removed from the stack.

In accordance with the above, an improved tray is disclosed that can be used as a standard in the fields of medicine, biotech, pharmaceuticals and others where the advantages of different types of plastic can be utilized to their fullest extent. Indeed, the versatility of the inventive tray fulfills the storage and handling needs of many fields including those requiring sterile conditions.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the breadth and scope of the description of the invention and the drawings here appended.

I claim:

1. Tray apparatus for storage of medical paraphernalia comprising
    a bottom plate,
    two side plates, each connected to a back plate, said two side plates and said back plate connected to said bottom plate at substantially right angles, forming a tray having an open top and an open front,
    said two side plates having at least one pair of oppositely positioned grooves extending at a substantially right angle to said bottom plate,
    a first front plate fitted within one pair of said at least one pair of oppositely positioned grooves,
    a removably attachable cover comprising a top plate and a vertically extending second front plate, said top plate covering said open top of said tray, said second front plate covering said open front of said tray.

2. The tray apparatus of claim 1 wherein said at least one pair of oppositely disposed grooves in said side plates extend from an upper surface of said side plates and end a distance above said bottom plate.

3. The tray apparatus of claim 1 wherein said tray includes a ledge extending around an upper edge of said two side plates and said back plate, said cover resting on said ledge.

4. The tray apparatus of claim 1 including a first extending tab on said cover having an opening therethrough, and a second tab extending from said ledge on said back plate, said second extending tab having an opening therethrough, said tab openings being in registry with each other when said cover is fitted to said tray.

5. The tray apparatus of claim 4 including locking apparatus fitted within said tab openings.

6. The tray apparatus of claim 1 wherein said at least one pair of oppositely disposed grooves have an "L" shaped cross sectional configuration and wherein said first front plate has a pair of grooves extending parallel to side edges of said first front plate and spaced an appropriate distance from said side edges so as to removably fit said first front plate in said "L" shape grooves.

7. The tray apparatus of claim 6 including a second pair of oppositely disposed grooves in said side plates, said second pair of grooves extending at a substantially right angle to said bottom plate, and a first dividing plate removably fitted within said second pair of oppositely disposed grooves, said dividing plate extending across said side plates.

8. The tray apparatus of claim 7 including a third pair of oppositely disposed grooves in said first front plate and said first dividing plate, and a second dividing plate extending between said third pair of oppositely disposed grooves, said second dividing plate being substantially perpendicular to said first front plate and said first dividing plate.

9. The tray apparatus of claim 7 including a third pair of oppositely disposed grooves in said side plates, said third pair of grooves extending at a substantially right angle to said bottom plate, and a second dividing plate removably fitted within said third pair of oppositely disposed grooves, said second dividing plate extending across said side plates.

10. The tray apparatus of claim 9 including a fourth pair of oppositely disposed grooves in said first dividing plate and said second dividing plate, said fourth pair of grooves extending at a substantially right angle to said bottom plate, and a third dividing plate removably extending between said fourth pair of oppositely disposed grooves.

11. Tray apparatus for storage of medical paraphernalia comprising
    a bottom plate,
    two side plates, each connected to a back plate, said two side plates and said back plate connected to said bottom plate at substantially right angles, forming a tray having an open top and an open front,
    said two side plates having at least one pair of oppositely positioned grooves extending at a substantially right angle to said bottom plate,
    a first front plate fitted within said one of at least one pair of grooves,
    a removably attachable cover comprising a top plate and a vertically extending second front plate, said top plate covering said open top of said tray, said second front plate covering said open front of said tray,
    said tray including a ledge extending around an upper edge of said two side plates and said back plate, said cover resting on said ledge,
    said tray and cover apparatus including a first extending tab on said cover having an opening therethrough, and a second tab extending from said ledge on said back plate, said second extending tab having an opening therethrough, said tab openings being in registry with each other when said cover is fitted to said tray.

12. Tray apparatus for storage of medical paraphernalia comprising
    at least two trays, each tray including
    a bottom plate,
    two side plates, each connected to a back plate, said two side plates and said back plate connected to said bottom plate at substantially right angles, forming a tray having an open top and an open front,
    said two side plates having at least one pair of oppositely positioned grooves extending at a substantially right angle to said bottom plate,
    a front plate removably fitted within said one of at least one pair of grooves,
    a ledge extending around an upper edge of said two side plates and said back plate,
    wherein a first of said at least two trays rests on said ledge of a second tray of said at least two trays so as to form at least two stacked trays.

* * * * *